United States Patent [19]

Suzuki et al.

[11] Patent Number: 5,248,684
[45] Date of Patent: Sep. 28, 1993

[54] CERTAIN 2-OXO-QUINOLINE CARBOXYLATES OR CORRESPONDING CARBOXAMIDES USEFUL AS ANTI-EMETICS AND SUPPRESSANTS OF MIGRAINE

[75] Inventors: Fumio Suzuki, Mishima; Hiroaki Hayashi, Shizuoka; Yoshikazu Miwa, Shizuoka; Akio Ishii, Shizuoka; Shunji Ichikawa, Shizuoka; Ichiro Miki, Shizuoka, all of Japan

[73] Assignee: Kyowa Hakko Kogyo Co., Ltd., Tokyo, Japan

[21] Appl. No.: 703,849

[22] Filed: May 21, 1991

[30] Foreign Application Priority Data

May 23, 1990 [JP] Japan .................. 2-133321

[51] Int. Cl.$^5$ ............ A61K 31/46; A61K 31/47; C07D 451/06; C07D 451/14
[52] U.S. Cl. .................. 514/299; 514/304; 546/112; 546/126
[58] Field of Search .............. 514/299, 304; 546/112, 546/126

[56] References Cited

U.S. PATENT DOCUMENTS 5,096,901  3/1992  Ward et al. .............. 514/214

FOREIGN PATENT DOCUMENTS 0200444  11/1986  European Pat. Off. ........... 546/125
0261964  3/1988  European Pat. Off. ........... 546/112
0307172  3/1989  European Pat. Off. ........... 546/112
0313393  4/1989  European Pat. Off. ........... 544/63
0309423  6/1989  European Pat. Off. ........... 546/125
0323077  7/1989  European Pat. Off. ........... 546/135
WO85/01048  3/1984  PCT Int'l Appl. ........... 546/135

OTHER PUBLICATIONS

Journal of Heterocyclic Chemistry, vol. 16, Dec. 1979, pp. 1605–1610, G. M. Coppola, et al.
Chemische Berichte, vol. 96, pp. 1234–1255; B. Eistert, et al (1963).
Journal of the American Society, vol>79, No. 15, pp. 4194–4198, S. Archer, et al. (Aug. 1957).

*Primary Examiner*—Alan L. Rotman
*Attorney, Agent, or Firm*—Antonelli, Terry Stout & Kraus

[57] ABSTRACT

There is disclosed a heterocyclic compound represented by general formula:

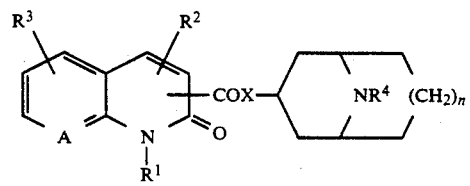

wherein $R^1$ represents hydrogen, lower alkyl or aryl; $R^2$ represents hydrogen, hydroxyl or lower alkyl; A represents CH or N; X represents —O— or —NH—; $R^3$ represents hydrogen, hydroxyl or lower alkyl; $R^4$ represents lower alkyl; represents 0 or 1, or a pharmaceutically acceptable salt thereof.

6 Claims, No Drawings

CERTAIN 2-OXO-QUINOLINE CARBOXYLATES OR CORRESPONDING CARBOXAMIDES USEFUL AS ANTI-EMETICS AND SUPPRESSANTS OF MIGRAINE

BACKGROUND OF THE INVENTION

The present invention relates to heterocyclic compounds having a serotonin-3 (hereafter referred to as 5-HT$_3$) antagonizing activity which compounds are useful as antiemetics and suppressants of migraine.

It is known that 5-HT$_3$ antagonists exhibit an antiemetic activity, an antianxious activity, a suppressing activity of mental disorders, a suppressing activity of migraine, etc. [Trends in Pharmacological Sciences, 8, 501 (1987); hereafter referred to as TIPS]. 5-HT$_3$ antagonists are effective against carcinostatic agent-induced vomiting, which has not been cured by dopamine antagonists. The 5-HT$_3$ antagonists are thus expected to be antiemetics of new type [Br. J. Cancer, 56, 159 (1987)].

As 5-HT$_3$ antagonists, an indole derivative ICS205-930:

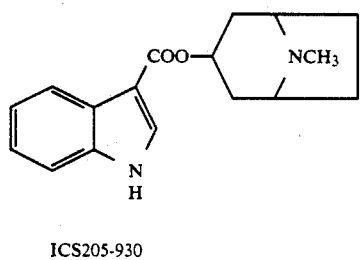

ICS205-930 an indazole derivative, BRL43694:

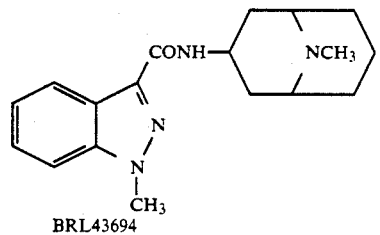

BRL43694 and the like are described in TIPS supra.

It is disclosed in Japanese Published Unexamined Patent Application No. 72886/85 (U.S. Pat. No. 4,797,406, GB-B-2145416) that quinoline derivatives represented by formula (A):

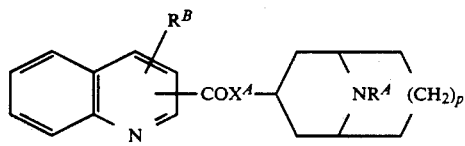

wherein $R^A$ represents lower alkyl (C$_1$-C$_7$); $R^B$ represents hydrogen or lower alkyl (C$_1$-C$_4$); $X^1$ represents —O— or —NH—; and P represents 0 or 1, possess a 5-HT$_3$ antagonizing activity and an antiarrhythmic activity. It is also disclosed in Japanese Published Unexamined Patent Application No. 4142988 (GB-A-2193633) that the above compounds represented by formula (A) are effective against vomiting caused by carcinostatic agents such as Cisplatin. It is further disclosed in Japanese Published Unexamined Patent Application No. 203365/89 (U.S. Pat. No. 4,983,600, EP-A-323077) that quinoline derivatives represented by formula (B):

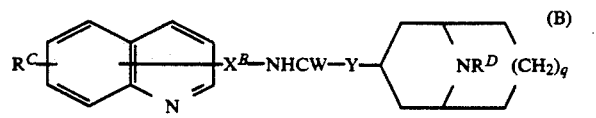

wherein $R^C$ represents hydrogen or hydroxyl; $X^B$ represents a single bond or CO; W represents oxygen or sulfur; Y represents NH or O; $R^D$ represents lower alkyl (C$_1$-$_6$); and q represents 0 or 1, are useful as 5-HT$_3$ antagonists.

SUMMARY OF THE INVENTION

An object of the present invention is to provide novel 2-quinolone derivatives and 1,8-naphthyridin-2-one derivatives, both of which have a 5-HT$_3$ antagonizing activity.

In accordance with the present invention, there is provided heterocyclic compounds represented by general formula (I):

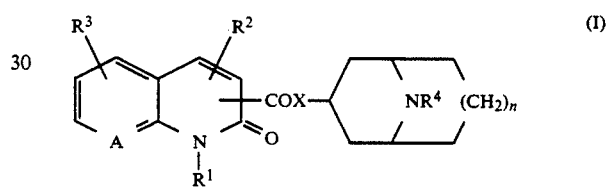

wherein $R^1$ represents hydrogen, lower alkyl or aryl; $R^2$ represents hydrogen, hydroxyl or lower alkyl; A represents CH or N; X represents —O— or —NH—; $R^3$ represents hydrogen, hydroxyl or lower alkyl; $R^4$ represents lower alkyl; and n represents 0 or 1, or a pharmaceutically acceptable salt thereof.

DETAILED DESCRIPTION OF THE INVENTION

In the definition of each group in formula (I), the lower alkyl means a straight or branched alkyl having 1 to 6 carbon atoms and includes, for example, methyl, ethyl, propyl, isopropyl, butyl, isobutyl, sec-butyl, tert-butyl, pentyl, neopentyl, hexyl, etc. The aryl means an aryl group having 6 to 10 carbon atoms such as phenyl, naphthyl, etc.

The salt of Compound (I) includes acid addition salts, metal salts, amino acid addition salts, etc. all of which are pharmaceutically acceptable.

As the pharmaceutically acceptable acid addition salt of Compound (I), mention may be made of inorganic acid salts such as hydrochlorides, sulfates, phosphates, etc.; organic acid salts such as acetates, maleates, fumarates, tartarates, citrates, etc. As the pharmaceutically acceptable metal salts, mention may be made of alkali metal salts such as sodium salts, potassium salts and alkaline earth metal salts such as magnesium salts, calcium salts, etc. In addition to these salts, there are mentioned aluminum salts and zinc salts. As the pharmaceutically acceptable amino acid salts, mention may be made of addition salts to lysine, glycine, phenylalanine, etc.

The processes for preparing Compound (I) are described below.

In the following processes, where the defined group changes under conditions given or is inappropriate for practicing the processes, the group may be treated in a manner conventional to organic synthetic chemistry, for example, protection of a functional group, removal of the protection, etc. so that the processes may be easily carried out.

Compound (I) can be obtained by reacting Compound (II) with Compound (III) in a solvent, preferably in the presence of a base, according to the following reaction.

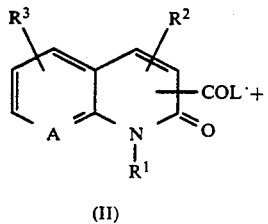

(II)

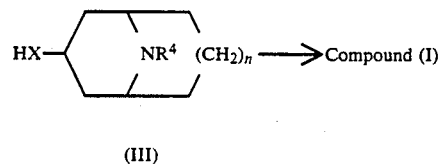

(III)

wherein $R^1$, $R^2$, $R^3$, $R^4$, A, X and n have the same significances as defined above; and L represents a leaving group.

Herein, the leaving group denoted by L refers to halogen such as chlorine, bromine, iodine, etc.; alkoxy such as methoxy, ethoxy, etc.; aryloxy such as phenoxy, etc.; alkoxycarbonyloxy such as ethoxycarbonyloxy, etc.; aroyloxy such as benzoyloxy, etc.

Compound (II) can be prepared in a conventional manner, for example, the method as described in J. Org. Chem., 39, 1803 (1974). Compound (III) is commercially available or can be prepared by the method as described in J. Am. Chem. Soc., 79, 4194 (1957).

As the reaction solvent, any solvent may be used singly or in combination, so long as it is inert to the reaction. Mention may be made of ethers such as tetrahydrofuran, dioxane, etc.; amides such as dimethylformamide, dimethylacetamide, etc.; ketones such as acetone, methyl ethyl ketone, etc.; alcohols such as methanol, ethanol, isopropyl alcohol, etc.; halogenated hydrocarbons such as methylene chloride, chloroform, dichloroethane, etc.; esters such as ethyl acetate, etc.; aromatic hydrocarbons such as benzene, toluene, xylene, etc.; and dimethylsulfoxide, etc. As the base used in the reaction, mention may be made of alkali metal bicarbonates such as sodium bicarbonate, potassium bicarbonate, etc.; alkali metal carbonates such as sodium carbonate, potassium carbonate, etc.; alkali metal hydrides such as sodium hydride, etc.; alkali metal alkoxides such as sodium methoxide, sodium ethoxide, etc.; alkali metal salts such as n-butyl lithium, etc.

The reaction is carried out at $-30°$ to $150°$ C., preferably at $10°$ to $100°$ C. and generally completed in 30 minutes to 20 hours.

The intermediates and the desired products in the processes described above may be isolated and purified by subjecting these compounds to purification means conventionally used in organic synthetic chemistry, for example, filtration, extraction, washing, drying, concentration, recrystallization, various chromatographies, etc. The intermediates may also be provided for the next reaction without particularly purifying them.

Where it is desired to obtained the salts of Compound (I), Compound (I) may be purified as it is in case that Compound (I) is obtained in a form of salt. In case that Compound (I) is obtained in a free form, the salts may be formed in a conventional manner.

Compound (I) and its pharmaceutically acceptable salts may also be present in the form of addition products to water or various solvents. These addition products are also included in the present invention.

Furthermore, Compound (I) includes all possible steric isomers including its optical isomers and a mixture thereof.

Specific examples of Compound (I) obtained in the process described above are shown in Table 1.

TABLE 1

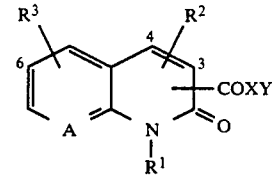

| Compound No. | A | $R^1$ | $R^2$ | $R^3$ | —COXY |
|---|---|---|---|---|---|
| 1 | CH | $(CH_2)_3CH_3$ | H | H | 4-COOE |
| 2 | CH | $(CH_2)_3CH_3$ | H | H | 4-COOE |
| 3 | CH | $CH(CH_3)_2$ | H | H | 4-COOE |
| 4 | CH | $CH_3$ | H | H | 4-COOE |
| 5 | CH | H | H | H | 4-COOE |
| 6 | CH | $(CH_2)_3CH_3$ | H | H | 4-CONHE |
| 7 | CH | $(CH_2)_2CH_3$ | H | H | 4-CONHE |
| 8 | CH | $CH_3$ | H | H | 4-CONHE |
| 9 | CH | $(CH_2)_3CH_3$ | H | H | 4-CONHF |
| 10 | CH | $(CH_2)_3CH_3$ | H | H | 4-CONHG |
| 11 | CH | $(CH_2)_3CH_3$ | 4-OH | H | 3-CONHE |
| 12 | N | Ph | 4-OH | H | 3-CONHE |
| 13 | CH | $CH_2CH_3$ | H | H | 4-COOE |
| 14 | CH | $CH_2CH(CH_3)_2$ | H | H | 4-COOE |
| 15 | CH | $(CH_2)_2CH(CH_3)_2$ | H | H | 4-COOE |

TABLE 1-continued

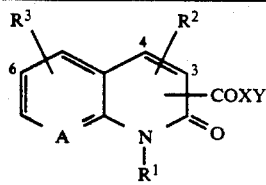

| Compound No. | A | R¹ | R² | R³ | —COXY |
|---|---|---|---|---|---|
| 16 | CH | (CH₂)₄CH₃ | H | H | 4-COOE |
| 17 | CH | (CH₂)₅CH₃ | H | H | 4-COOE |
| 18 | CH | CH₂Ph | H | H | 4-COOE |
| 19 | CH | Ph | H | H | 4-COOE |
| 20 | CH | (CH₂)₃CH₃ | 3-CH₂CH₃ | H | 4-COOE |
| 21 | CH | (CH₂)₃CH₃ | H | 6-CH₃ | 4-COOE |
| 22 | N | (CH₂)₃CH₃ | 4-OH | H | 3-COOE |
| 23 | CH | (CH₂)₃CH₃ | 4-OH | H | 3-COOE |
| 24 | N | Ph | 4-OH | H | 3-COOE |
| 25 | CH | H | H | H | 4-CONHE |
| 26 | CH | (CH₂)₃CH₃ | 3-CH₂CH₃ | H | 4-CONHE |
| 27 | CH | Ph | H | H | 4-CONHE |
| 28 | CH | CH₃ | 3-OH | H | 4-CONHE |
| 29 | CH | (CH₂)₃CH₃ | 3-OH | H | 4-CONHE |
| 30 | CH | Ph | 4-OH | H | 3-CONHE |
| 31 | CH | Ph | 4-OH | H | 3-CONHG |
| 32 | N | (CH₂)₃CH₃ | 4-OH | H | 3-CONHE |
| 33 | CH | H | 4-OH | H | 3-COOE |
| 34 | CH | H | 4-OH | H | 3-CONHE |
| 35 | CH | H | 4-OH | H | 3-CONHG |

Note
Ph: phenyl

E: 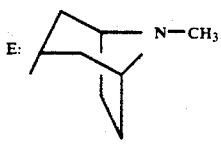

F: 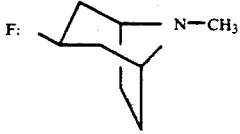

G: 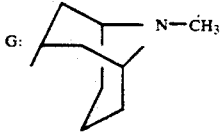

The pharmacological activities of Compound (I) are illustrated by referring to test examples.

a) 5-HT₃ Receptor binding test

Using rat neutroblastoma-glyoma NG108-15 cell membrane fraction, the binding activities of the test compounds to 5-HT₃ receptor were examined.

A membrane fraction of NG108-15 cells was prepared according to the method of Neijt et al. [Naunyn-Schmiedeberg's Arch. Pbarmacol., 337, 493 (1988)].

The receptor binding experiment was performed using [³H] quipazine (J. Neurochem., 52, 1787 (1989)], a high affinity ligand to 5-HT₃ receptor.

A membrane fraction obtained from 3×10⁵ NG108-15 cells was suspended in 1 ml of 20 mM Tris-hydrochloride buffer (pH 7.5) (hereafter referred to as Buffer) containing 154 MM sodium chloride. Then, 2 nM [3H] quipazine (2519.7 GBq/mmol; Du Pont Co., Ltd.) and various concentrations of the test compound were added to the suspension followed by incubating at 37° C. for 60 minutes. 4 ml of ice-cold Buffer was added to terminate the reaction and then the mixture was filtered through GF/C glass fiber filter (Whatmann Co., Ltd.). The filter was washed 5 times with 2 mi of ice-cold Buffer, and put in a scintillation vial containing 8 mi of Scintisol EX-H (Wako Pure Chemicals, Inc.). Radioactivity on the filter was counted in a liquid scintillation counter (TRI-CARB 2200C.A; Packard Co., Ltd.).

An inhibition of the [³H] quipazine binding for the test compound was estimated according to the equation;

Inhibition rate (%) =

$$\left(1 - \frac{\text{binding in the presence of test compound} - \text{non-specific binding}}{\text{total binding} - \text{non-specific binding}}\right) \times 100$$

"Total binding" is [3H] quipazine-binding in the absence of test compound and "non-specific binding" is [³H] quipazine-binding in the presence of 10 PM MDL7222 5-HT₃ antagonist [Naunyn-Schmiedeberg's Arch. Pharmacol., 326, 36 (1984)].

The results are shown in Table 2.

TABLE 2

| Compound | Inhibition (%) | |
|---|---|---|
| | $10^{-7}$M | $10^{-8}$M |
| 1Sa* | 113 | |
| 2Sa | 101 | 98 |
| 3Sa | 96 | 99 |
| 4Sa | | 76 |
| 5Sa | 97 | 72 |
| 6Sa | 66 | 12 |
| 11Sa | 101 | 96 |
| 12Sa | 80 | 32 |
| 13Sa | 101 | 90 |
| 14Sa | 105 | 97 |
| 15Sa | 108 | 95 |
| 16Sa | 103 | 89 |
| 17Sa | 101 | 86 |
| 18Sa | 103 | 91 |
| 19Sa | 101 | 96 |
| 30Sa | 100 | 91 |
| 31Sa | 92 | 60 |
| contrast compound** | 84 | 12 |

*Sa indicates a salt of the compound.
**Contrast compound is represented by the following formula:

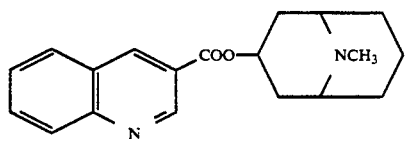

[U.S. Pat. No. 4,797,406; GB-B-2145416]

b) Activity against CisPlatin-induced vomiting

Female and male *Suncus murinus* animals weighing 23 to 68 g were used, one group consisting of 5 to 10 animals. According to the method of Matsuki et al. (Japan J. Pharmacol., 48, 303 (1988)], the animals were isolated in metal mesh cage (one animal/one cage). One hour after, the test compound or physiological saline (control) was intraperitoneally administered (i.p.) in a volume of 0.1 ml/10 g of body weight. Further 30 minutes after administration of the test compound, Cisplatin (40 mg/kg) was intraperitoneally administered. After administration of Cisplatin, a time period (latency) for the first vomiting and the number of frequencies (episodes) of vomiting caused in the period of 5 to 120 minutes after administration were determined. The latency and the number of frequencies in the test compound administered group were compared with those in the control group. The test of significance was performed by Student's t-test.

The results are shown in Table 3.

TABLE 3

| Compound No. | Dose (mg/kg i.p.) | Number of Vomiting (Episodes) (mean ± S.E.M.) | Latency (min.) (mean ± S.E.M.) |
|---|---|---|---|
| Control | — | 28.0 ± 6.7 | 35.1 ± 4.4 |
| Compound 1Sa | 0.1 | 18.0 ± 1.6 | 44.3 ± 2.0 |
| | 0.5 | 6.8 ± 2.0* | 71.5 ± 12.9* |

*p < 0.05.

c) Acute toxicity

The test compound was orally and intraperitoneally administered to ddY strain male mice weighing 20 to 25 g. MLD (Minimum Lethal Dose) was determined by observing the mortality for 7 days after the administration. The results are shown in Table 4.

TABLE 4

| Compound No. | MLD (mg/kg) | |
|---|---|---|
| | i.p. | p.o. |
| 1Sa | 100 | 200 |
| 2Sa | 100 | 200 |
| 3Sa | 100 | 200 |
| 6Sa | >100 | >300 |
| 7Sa | >100 | >300 |
| 8Sa | >100 | >300 |
| 9Sa | 100 | >300 |
| 10Sa | 100 | 300 |
| 11Sa | >100 | >300 |
| 13Sa | 100 | 200 |
| 14Sa | 50 | 200 |
| 15Sa | 100 | 300 |
| 16Sa | 100 | 300 |
| 17Sa | 100 | >300 |
| 18Sa | 100 | >300 |
| 19Sa | 100 | 200 |
| 20Sa | 100 | 200 |
| 24Sa | >100 | >300 |
| 29Sa | >100 | >300 |
| 30Sa | 100 | >300 |
| 32Sa | 100 | >300 |

These results suggest that Compound (I) has an excellent 5-HT$_3$ antagonizing activity and is useful for the treatment of nausea and vomiting which are side effects caused by chemotherapy and radiotherapy of cancer, and for the treatment of anxiety, mental disorders (for example, schizophrenia and mania), migraine, pains, etc.

Compound (I) or a pharmaceutically acceptable salt thereof may be used as it is or in various preparation forms. The pharmaceutical composition of the present invention can be prepared by uniformly mixing Compound (I) or a pharmaceutically acceptable salt; thereof with pharmaceutically acceptable carriers. The pharmaceutical composition may be desirably in a single dose unit which is suited for oral or parenteral administration.

In preparing the composition in an oral administration form, any pharmaceutically acceptable carriers may be used. Liquid preparations for oral administration, for example, a suspension and a syrup, may be prepared using water; sugars such as sucrose, sorbitol, fructose, etc.; glycols such as polyethylene glycol, propylene glycol, etc.; oils such as sesami oil, olive oil, soybean oil, etc.; preservative such as alkyl p-hydroxybenzoic acid esters, etc.; flavors such as strawberry flavor, peppermint, etc. Powders, pills capsules and tablets may be prepared using excipients such as lactose, glucose, sucrose, mannitol, etc.; disintegrators such as starch, sodium alginate, etc.; lubricants such as magnesium stearate, talc, etc.; binders such as polyvinyl alcohol, hydroxypropyl cellulose, gelatin, etc.; surfactants such as fatty acid esters, etc.; plasticizers such as glycerine, etc. Tablets and capsules are the most useful single dose unit for oral administration since their administration is easy. When tablets or capsules are prepared, solid pharmaceutical carriers are used. Furthermore, a solution for parenteral administration may be prepared using carriers composed of distilled water, saline, a glucose solution or a mixture of saline and a glucose solution.

The effective dose of Compound (I) or its pharmaceutically acceptable salt and the number of administration may vary depending upon form of administration, age, body weight, condition, etc. of a patient but it is generally preferred to administer in a dose of 0.01 to 25 mg/kg/day by dividing into 3 to 4 times.

In addition, Compound (I) may also be administered by inhalation in the form of aerosol, finely divided powders or spray solution. When administered in the form of aerosol, the present compound is dissolved in an appropriate solvent which is pharmaceutically acceptable, for example, ethyl alcohol or in combination with a miscible solvent and the resulting solution may be mixed with a pharmaceutically acceptable propellant. Such aerosol composition is filled up in a pressure container equipped with an aerosol valve suited to release a pressurized composition, which is then provided for use.

Hereafter the examples of the present invention and reference examples are given.

EXAMPLE 1

Endo-(8-methyl-8-azabicyclo[3.2.1]oct-3-yl)-1-(n-butyl)-2-oxo-1,2-dihydro-4-quinolinecarboxylate (Compound 1)

A mixture of 5.00 g (20.4 mmols) of Compound a obtained in Reference Example 1 and 40 ml of thionyl chloride was heated to reflux for 30 minutes. After concentration under reduced pressure, 80 mg of anhydrous tetrahydrofuran was added to the concentrate followed by stirring (Solution A).

A mixture of 3.11 g (22.0 mmols) of tropine and 15 ml of anhydrous tetrahydrofuran was stirred at 0° C. under an argon atmosphere. 13.6 ml (22.0 mmols) of 15% n-butyl lithium-hexane solution was added to the mixture followed by stirring at 0° C. for further 15 minutes. After concentration under reduced pressure, 20 ml of anhydrous tetrahydrofuran and the Solution A were dropwise added to the concentrate under an argon atmosphere. The mixture was stirred at 0° C. for an hour. After concentration under reduced pressure, a small quantity of methanol and water were added to the concentrate followed by extraction with chloroform. After drying over anhydrous sodium sulfate, the solvent was evaporated under reduced pressure. The residue was purified by silica gel column chromatography (eluting solvent: chloroform/reethanol=10/1). The resulting product was dissolved in chloroform and ethyl acetate solution saturated with hydrogen chloride was added to the solution. The solution was poured onto cold diethyl ether and the precipitated crystals were filtered and dried to give 3.12 g (yield: 37.8%) of Compound 1 as the hydrochloride.

Melting point: 80°–86° C.
MS (EI) m/e 368 (M+)
IR(KBR) cm$^{-1}$: 1727, 1650, 1584, 1447, 1228, 1025, 762
NMR(DMSO-d$_6$) δ(ppm): 8.21 (1H, d, J=8.1Hz), 7.60~7.81 (2H, m), 7.34 (1H, m), 7.05 (1H, s), 5.28 (1H, m), 4.28 (2H, t, J=7.6Hz), 3.88 (2H, m), 2.0~2.9 (11H, m), 1.62 (2H, m), 1.41 (2H, m), 0.94 (3H, t, J=7.3Hz)

EXAMPLE 2

Endo-(8-methyl-B-azabicyclo[3.2.1]oct-3-yl)2-oxo-1-(n-propyl)-1,2-dihydro-4-quinolinecarboxylate (Compound 2)

2-Oxo-1-(n-propyl)-1,2-dihydro-4-quinolinecarboxylic acid was obtained in a manner similar to Reference Example 1 except for using n-propyl iodide in place of n-butyl iodide (yield: 62%, 68%).

The carboxylic acid was used instead of Compound a and treated in a manner similar to Example 1 to give Compound 2 as the hydrochloride (yield: 48%).

Melting point: 273.0°–274.5° C.
MS (EI) m/e: 354 (M+)
IR(KBR) cm$^{-1}$: 1720, 1657, 1590, 1451, 1241, 1228, 1021, 783, 747
NMR(DMSO-d$_6$) δ(ppm): 10.91 (1H, brs), 8.21 (1H, d, J=8.3Hz), 7.53~7.82 (2H, m), 7.34 (1H, m), 7.05 (1H, s), 5.28 (1H, m), 4.25 (2H, J=7.7Hz), 3.89 (2H, m) 2.67 (3H, s) 1.9~2.9 (8H, m), 1.67 (2H, m), 0.97 (3H, J=7.4Hz)

EXAMPLE 3

Endo-(8-methyl-8-azabicyclo[3.2.1]oct-3-yl)l-isopropyl-2-oxo-1,2-dihydro-4-quinolinecarboxylate (Compound 3)

-Isopropyl-2-oxo-1,2-dihydro-4-quinoline carboxylic acid was obtained in a manner similar to Reference Example 1 except for using isopropyl bromide in place of n-butyl iodide and changing the reaction time from one day to 5 hours, and the reaction temperature from room temperature to 80° C. (yield: 4%, 98%).

The carboxylic acid was used instead of Compound a and treated in a manner similar to Example 1 to give Compound 3 as the hydrochloride (yield: 37%).

Melting point: 244.0°–244.50° C.
MS (EI) m/e: 354 (M+)
IR(KBr) cm$^{-1}$: 1727, 1651, 1590, 1445, 1218, 1026, 794, 762
NMR(DMSO-d$_6$) δ(ppm): 10.88 (1H, brs), 8.18 (1H, d, J=8.2Hz), 7.84 (1H, d, J=8.8Hz), 7.67 (1H, m), 7.32 (1H, m), 6.97 (1H, s), 5.36 (1H, m), 5.27 (1H, m) 3.89 (2H, m) 2.67 (3H, s), 1.95~2.90 (8H, m), 1.57 (6H, d, J=6.8Hz)

EXAMPLE 4

Endo-(8-methyl-8-azabicyclo[3.2.1]oct-3-yl)l-methyl-2-oxo-1,2-dihyro-4-quinolinecarboxylate (Compound 4)

1-Methyl-2-oxo-1,2-dihydro-4-quinolinecarboxylic acid was obtained in a manner similar to Reference Example 1 except for using methyl iodide in place of n-butyl iodide (yield: 96%, 100%) .

The carboxylic acid was used instead of Compound a and treated in a manner similar to Example 1 to give Compound 4 as the hydrochloride (yield: 18%).

Melting point: 279.0°–282.0° C.
MS (EI) m/e: 326 (M+)
IR(KBr) cm$^{-1}$: 1722, 1651, 1588, 1450, 1250, 1027, 780, 748
NMR(DMSO-d$_6$) δ(ppm): 10.93 (1H, brs), 8.21 (1H, d, J=8.4Hz), 7.72 (1H, m), 7.64 (1H, d, J=8.7Hz), 7.35 (1H, m), 7.06 (1H, s), 5.28 (1H, m) 3.89 (2H, m), 3.67 (3H, s), 2.67 (3H, s), 1.95~2.95 (8H, m)

EXAMPLE 5

Endo-(8-methyl-8-azabicyclo[3.2.1]oct-3-yl)2-hydroxy-4-quinolinecarboxylate (Compound 5)

Compound 5 was obtained as the hydrochloride in a manner similar to Example 1 except for using 2-hydroxy-4-quinolinecarboxylic acid in place of Compound a and changing the reaction time from an hour to 3 hours (yield: 6%).

Melting point: 303.0°–306.0° C.
MS (EI) m/e: 312 (M−)
IR(KBr) cm$^{-1}$: 1734, 1666, 1548, 1434, 1217, 1027, 788, 762
NMR((DMSO-d$_6$) δ(ppm): 12.16 (1H, brs), 10.88 (1H, brs), 8.16 (1H, d, J=7.3 Hz), 7.58 (1H, m), 7.42

(1H, d, J=7.6Hz), 7.25 (1H, m), 6.96 (1H, s), 5.26 (1H, m), 3.89 (2H, m), 2.67 (3H, s), 1.95~2.90 (8H, m)

EXAMPLE 6

Endo-N-(8-methyl-8-azabicyclo[3.2.1]oct-3-yl)-1-(n-butyl)-2-oxo-1,2-dihydro-4-quinolinecarboxamide (Compound 6)

A mixture of 1.23 g (5.01 mmols) of Compound a obtained in Reference Example 1 and 10 ml of thionyl chloride was heated to reflux for 30 minutes and then concentrated under reduced pressure (Solid B).

A solution (40 ml) of 12.0 mg (5.00 mmols) of sodium hydride in anhydrous tetrahydrofuran was stirred at room temperature under an argon atmosphere. 20 ml of a solution of 0.70 g (4.99 mmols) of Endo-8-methyl-8-azabicyclo[3.2.1]oct-3-yl-amine [J. Am. Chem. Soc., 79, 4194 (1957)] in anhydrous tetrahydrofuran was added to the mixture followed by stirring at room temperature for further an hour. Solid B was slowly added to the solution and the mixture was stirred at room temperature for 2 hours. After completion of the reaction, the solution was added to an aqueous 1N hydrochloric acid solution. The mixture was washed twice with chloroform. An aqueous saturated sodium bicarbonate solution was added to the aqueous layer to render the layer weak alkaline. Thereafter, the system was extracted twice with chloroform. The chloroform layer was collected and dried over anhydrous sodium sulfate. The solvent was then evaporated under reduced pressure. After 35 ml of water was added to the residue, the precipitated crystals were filtered and dried to give 0.92 g (yield, 50%) of Compound 6.

After 0.26 g (2.24 mmols) of fumaric acid was added to 40 ml of a solution of 0.90 g of Compound 6 in isopropyl alcohol, the mixture was stirred at room temperature. To the solution was added 15 ml of n-hexane at room temperature while stirring. The precipitated crystals were filtered and dried to give 0.85 g (yield: 72%) of Compound 6 as the fumarate.

Melting point: 217.8°-219.0° C.

MS (EI) m/e: 367 (M+)

IR(KBr) cm$^{-1}$: 3420 (br), 1708, 1642, 1583, 1451, 1297, 981, 755

NMR(DMSO-d$_6$) δ(ppm) 8.67 (1H, J=4.2Hz), 7.55~7.85 (3H, m), 7.29 (1H, m), 6.57 (1H, s), 6.53 (2H, s), 4.27 (2H, t, J=7.5Hz), 4.03 (1H, m), 3.64 (2H, m), 2.57 (3H, s) 1.9~2.5 (8H, m), 1.60 (2H, m) 1.41 (2H, m), 0.94 (3H, t , J=7.2Hz)

EXAMPLE 7

Endo-N-(8-methyl-8-azabicyclo[3.2.1]oct-3-yl)-1-(n-propyl)-2-oxo-1,2-dihydro-4-quinolinecarboxamide (Compound 7)

1-(n-Propyl)-2-oxo-1,2-dihydro-4-quinolinecarboxylic acid was obtained in a manner similar to Reference Example 1 except for using n-propyl iodide in place of n-butyl iodide (yield: 62%, 68%).

The carboxylic acid was used instead of Compound a and treated in a manner similar to Example 6 to give Compound 7 as the fumarate (yield: 35%, 64%).

Melting point: 239.7°-242.2° C.

MS (EI) m/e: 353 (M+)

IR(KBr) cm$^{-1}$: 3430(br), 1690, 1640, 1584, 1530, 1451, 1368, 1296, 1257, 1201, 1093, 987, 760

NMR (DMSO-d$_6$) δ(ppm) 8.62 ( 1H, d, J=4.4Hz), 7.50~7. 85 (3H, m), 7.28 (1H, m), 6.56 (1H, s), 6.51 (2H, s), 4.22 (2H, t, J=7.7Hz), 4.02 (1H, m), 3.53 (2H, m), 2.50 (3H, s), 1.9~2.5 ( 8H, m), 1.95 (2H, m), 0.98 (3H, t , J=7.4Hz)

EXAMPLE 8

Endo-N-(8-methyl-8-azabicyclo[3.2.1]oct-3-yl)-1-methyl-2-oxo-1,2-dihydro-4-quinolinecarboxamide (Compound 8)

1-Methyl-2-oxo-1,2-dihydro-4-quinolinecarboxylic acid was obtained in a manner similar to Reference Example 1 except for using methyl iodide in place of n-butyl iodide (yield: 96%, 100%).

The carboxylic acid was used instead of Compound a and treated in a manner similar to Example 6 to give Compound 8 as the fumarate (yield: 29%, 80%).

Melting point: 254.5°-255.5° C.

MS (EI) m/e: 325 (M+)

IR(KBR) cm$^{-1}$: 1656, 1636, 1586, 1539, 1456, 1374, 1198, 986, 751

NMR (DMSO-d$_6$) δ(ppm): 8.62 (1H, d, J=4.4Hz), 7.58~7.76 (3H, m), 7.30 (1H, m), 6.59 (1H, s), 6.51 (2H, s), 4.02 (1H, m), 3.65 (3H, s), 3.56 (2H, m), 2.51 (3H, s), 1.9~2.50 (8H, m)

EXAMPLE 9

Exo-N-(8-methyl-8-azabicyclo[3.2.1]oct-3-yl)-1-(n-butyl)-2-oxo-1,2-dihydro-4-quinolinecarboxamide (Compound 9)

Compound 9 was obtained as the fumarate in a manner similar to Example 6 except for using Exo-8-methyl-8-aza-bicyclo[3.2.1]oct-3-yl-amine (Japanese Published Unexamined Patent Application No. 28085/82) in place of Endo-8-methyl-8-azabicyclo[3.2.1]oct-3-yl-amine (yield: 32%, 52%).

Melting point: 127°-130° C.

MS (EI) m/e: 367 (M+)

IR(KBR) cm$^{-1}$: 3420(br), 1641, 1581, 1453, 983, 754

IR (DMSO-d$_6$) δ(ppm) 8.72 (1H, d, J=7.7Hz), 7.50~7.82 (3H, m), 7.27 (1H, m), 6.55 (1H, s), 6.52 (2H, s), 4.26 (2H, t, J=7.4Hz), 3.56 (2H, m), 2.48 (3H, s), 1.7~2.3 (8H, m) 1.60 (2H, m), 1.40 (2H, m), 0.94 (3H, t, J=7. 3Hz)

EXAMPLE 10

Endo-N-(9-methyl-9-azabicyclo[3.3.1]non-3-yl)-1-(n-butyl)-2-oxo-1,2-dihydro-4-quinolinecarboxamide (Compound 10)

Compound 10 was obtained as the fumarate in a manner similar to Example 6 except for using Endo-9-methyl-9-azabicyclo- 3.3.1]non-3-yl-amine (Japanese Published Unexamined Patent Application No. 67284/84) in place of Endo-8-methyl-8-azabicyclo-[3.2.1]oct-3-yl-amine (yield: 90%, 75%).

Melting point: 253.1 254.8° C.

MS (EI) m/e: 381 (M+)

. IR(KBr) cm$^{-1}$: 3440 (br), 1650, 1587, 1451, 1307, 878, 793

NMR (DMSO-d$_6$) δ(ppm): 8.79 (1H, d, J=6.4Hz), 7.78 (1H, d, J=8.1Hz) 7.57~7.74 (2H, m), 7.30 (1H, m), 6.65 (1H, s), 6.63 (2H, s) 4.52 (1H, m), 4.28 (2H, t, J=7.6Hz), 3.65 (2H, 2.84 (3H, s), 1.15~2.65 (14H, m), 0.94 (3H, t, J=7.3Hz)

EXAMPLE 11

Endo-N-(8-methyl-8-azabicyclo[3.2.1]oct-3-yl)-1-(n-butyl)-4-hydroxy-2-oxo-1,2-dihydro-3-quinolinecarboxamide (Compound 11)

A mixture of 1.45 g (5.01 mmols) of ethyl 1-(n-butyl)-4-hydroxy-2-oxo-1,2-dihydro-3-quinolinecarboxylate [J. Heterocyclic Chem., 16, 1605 (1979)], 1.05 g (7.49 mmols) of Endo-8-methyl-8-azabicyclo-[3.2.1]oct-3-yl-amine and 100 ml of xylene was stirred for 15 hours with heating at 110° C. After completion of the reaction, the solution was added to an aqueous 1N hydrochloric acid solution. The mixture was washed twice with chloroform. An aqueous saturated sodium bicarbonate solution was further added to the aqueous layer to render the layer weak alkaline. Thereafter, the system was extracted twice with chloroform. The chloroform layer was collected and dried over anhydrous sodium sulfate. The solvent was then distilled off under reduced pressure. After ethyl acetate was added to the residue, the precipitated crystals were filtered and dried to give 0.91 g (yield: 47%) of Compound 11.

After 0.27 g (2.33 mmols) of fumaric acid was added to 40 ml of a solution of 0.91 g of Compound 11 in isopropyl alcohol, the mixture was stirred at room temperature. To the solution was added 15 mi of n-hexane at room temperature while stirring. The precipitated crystals were filtered and dried to give 1.02 g (yield: 86%) of Compound 11 as the fumarate.

Melting point: 159.2–161.50° C.
MS (EI) m/e: 383 (M+)
IR(KBr) cm$^{-1}$: 3420(br), 1720, 1641, 1561, 1483, 1408, 1276, 1167, 977, 789, 778
NMR (DMSO-d$_6$) δ(ppm): 16.94 (1H, s), 13.06 (2H, brs), 11.07 (1H, d, J=7.3Hz), 8.11 (1H, d, J=8.1Hz), 7.82 (1H, m), 7.65 (1H, d, J=8.8Hz), 7.39 (1H, m), 6.64 (2H, s), 4.19 (1H, m) 4.28 (2H, t, J=7.5Hz), 3.89 (2H, m), 2.70 (3H, s), 1.8~2.9 (8H, m) 1.62 (2H, m), 1.41 (2H, m), 0.94 (3H, t, J=7.3Hz)

EXAMPLE 12

Endo-N-(8-methyl-8-azabicyclo[3.2.1]oct-3-yl)-4-hydroxy-2-oxo-1-phenyl-1,2-dihydro-1,8-naphthyridine-3-carboxamide (Compound 12)

Compound 12 was obtained as the fumarate in a manner similar to Example 11 except for using Compound e obtained in Reference Example 2 instead of ethyl 1-(n-butyl)-4-hydroxy-2-oxo-1,2-dihydro-3-quinolinecarboxylate. (yield: 60%, 81%)

Melting point: 146.7°–148.20° C.
MS (EI) m/e: 404 (M+)
IR(KBR) cm$^{-1}$: 3400(br), 1708, 1640, 1630, 1561, 1553, 1474, 1307, 982, 794, 736
NMR(DMSO-d$_6$) δ(ppm): 10.74 (1H, d, J=7.3Hz), 8.55H, d, J=4.6Hz) 8.49 (1H, d, J=7.9Hz), 7.1~7.7 (7H, m), 6.53 (2H, s), 4.15 (1H, m), 3.53 (2H, m), 2.48 (3H, m), 1.65~2.60 (8H, m),

EXAMPLE 13

Endo-(8-methyl-8-azabicyclo[3.2.1]oct-3-yl) 1-ethyl-2-oxo-1,2-dihydro-4-quinolinecarboxylate (Compound 13)

1-Ethyl-2-oxo-1,2-dihydro-4-quinolinecarboxylic acid was obtained (yield, 65%, 68%) in a manner similar to Reference Example 1 except for using ethyl iodide instead of n-butyl iodide. The obtained carboxylic acid in place of Compound a was treated in a manner similar to Example 1 to give Compound 13 as the hydrochloride (yield, 14%)

Melting point: 230.0°–232.0° C.
MS (EI) m/e: 340 (M−)
IR(KBr) cm$^{-1}$: 1725, 1651, 1644, 1587, 1445, 1219, 1027, 789, 748
NMR(DMSO-d$_6$) δ(ppm) 10.97 (1H, brs), 8.21 (1H, d, J=7.8Hz), 7.60~7.80 (2H, m), 7.35 (1H, m), 7.05 (1H, s), 5.27 (1H, m), 4.33 (2H, q, J=7.1Hz), 3.89 (2H, m), 2.67 (3H, d, J=5.1Hz), 1.95~2.80 (8H, m), 1.24 (3H, t, J=7.1Hz)

EXAMPLE 14

Endo-(8-methyl-8-azabicyclo[3.2.1]oct-3-yl) 1-isobutyl-2-oxo-1,2-dihydro-4-quinolinecarboxylate (Compound 14)

1-Isobutyl-2-oxo-1,2-dihydro-4-quinolinecarboxylic acid was obtained (yield, 6%, 100%) in a manner similar to Reference Example 1 except for using isobutyl bromide instead of n-butyl iodide, and changing the reaction time from one day to 5 hours and the reaction temperature from room temperature to 800° C. The obtained carboxylic acid in place of Compound a was treated in a manner similar to Example 1 to give Compound 14 as the hydrochloride (yield, 29%).

Melting point: 262.0°–263.50° C.
MS (EI) m/e: 368 (M+)
IR(KBR) cm$^{-1}$: 1721, 1658, 1652, 1590, 1450, 1240, 1025, 787, 753
NMR(DMSO-d$_6$) δ(ppm): 10.85 (1H, brs), 8.21 (1H, d, J=7.8Hz), 7.60~7.80 (2H, m), 7.34 (1H, m), 7.06 (1H, s), 5.28 (1H, m), 4.19 (2H, d) J=7.6Hz), 3.89 (2H, m), 2.67 (3H, d, J=4.6Hz), 1.90~2.80 (9H, m), 0.92 (6H, d, J=6.5Hz)

EXAMPLE 15

Endo-(8-methyl-8-azabicyclo[3.2.1]oct-3-yl) 1-isopentyl-2-oxo-1,2-dihydro-4-quinolinecarboxylate (Compound 15)

1-Isopentyl-2-oxo-1,2-dihydro-4-quinolinecarboxylic acid was obtained (yield, 44%, 100%) in a manner similar to Reference Example 1 except for using isopentyl iodide instead of n-butyl iodide. The carboxylic acid in place of Compound a was treated in a manner similar to Example 1 to give Compound 15 as the hydrochloride (yield, 28%).

Melting point: 68.5°–69.0° C.
MS (EI) m/e: 382 (M+)
IR(KBr) cm$^{-1}$: 1724, 1658, 1651, 1592, 1453, 1251, 1078, 1023, 783, 746
NMR(DMSO-d$_6$) δ(ppm): 10.89 (1H, brs), 8.21 (1H, d, J=8.1Hz), 7.72 (1H, m), 7.60 (1H, d, J=8.5Hz), 7.34 (1H, m), 7.04 (1H, s), 5.28 (1H, m), 4.30 (2H, t, J=7.8Hz), 3.87 (2H, m), 2.68 (3H, s), 2.00~2.85 (8H, m), 1.74 (1H, m), 1.51 (2H, m), 0.98 (6H, d, J=6.6Hz)

EXAMPLE 16

Endo-(8-methyl-8-azabicyclo[3.2.1]oct-3-yl)2-oxo-1-n-pentyl-1,2-dihydro-4-quinolinecarboxylate (Compound 16)

2-Oxo-1-(n-pentyl)-1,2-dihydro-4-quinolinecarboxylic acid was obtained (yield, 47%, 98%) in a manner similar to Reference Example 1 except for using n-pentyl bromide instead of n-butyl iodide, and changing the reaction time from one day to 5 hours and the reaction temperature from room temperature to 80° C. The obtained carboxylic acid in place of Compound a was treated in a manner similar to Example 1 to give Compound 16 as the hydrochloride (yield, 56%).
Melting point: 72.0°–75.0° C.
MS (EI) m/e: 382 (M+)
IR(KBr) cm$^{-1}$: 1723, 1658, 1651, 1592, 1452, 1246, 1225, 1023, 782, 745
NMR(DMSO-d$_6$) δ(ppm): 10.82 (1H, brs), 8.21 (1H, d, J=8.2Hz), 7.60~7.80 (2H, m), 7.34 (1H, m), 7.05 (1H, s), 5.28 (1H, m), 4.27 (2H, t, J=7.6Hz), 3.89 (2H, m), 2.67 (3H, d, J=5.1Hz), 2.00~2.80 (8H, m), 1.64 (2H, m), 1.20~1.50 (4H, m), 0.88 (3H, t, J=7.0Hz)

EXAMPLE 17

Endo-(8-methyl-8-azabicyclo[3.2.1]oct-3-yl) 1-(n-hexyl)-2-oxo-1,2-dihydro-4-quinolinecarboxylate (Compound 17)

1-(n-Hexyl)-2-oxo-1,2-dihydro-4-quinolinecarboxylic acid was obtained (yield, 46%, 99%) in a manner similar to Reference Example 1 except for using n-hexyl bromide instead of n-butyl iodide, and changing the reaction time from one day to 3 hours and the reaction temperature from room temperature to 80° C. The obtained carboxylic acid in place of Compound a was treated in a manner similar to Example 1 to give Compound 17 as the hydrochloride (yield, 42%).
Melting point: 146.5°–147.5° C.
MS (EI) m/e: 396 (M+)
IR(KBr) cm$^{-1}$: 1722, 1658, 1649, 1589, 1454, 1239, 1227, 1023, 784, 746
NMR(DMSO-d$_6$) δ(ppm) 10.90 (1H, brs), 8.21 (1H, d, J=8.1Hz), 7.55~7.80 (2H, m), 7.34 (1H, m), 7.05 (1H, s), 5.27 (1H, m), 4.27 (2H, t, J=7.7Hz), 3.89 (2H, m), 2.67 (3H, d, J=4.9Hz), 1.95~2.80 (8H, m), 1.63 (2H, m), 1.10~1.50 (6H, m), 0.87 (3H, t, J=7.1Hz)

EXAMPLE 18

Endo-(8-methyl-8-azabicyclo[3.2.1]oct-3-yl) 1-benzyl-2-oxo-1,2-dihydro-4-quinolinecarboxylate (Compound 18)

1-Benzyl-2-oxo-1,2-dihydro-4-quinolinecarboxylic acid was obtained (yield, 48%, 96%) in a manner similar to Reference Example 1 except for using benzyl bromide instead of n-butyl iodide. The obtained carboxylic acid in place of Compound a was treated in a manner similar to Example 1 to give Compound 18 as the hydrochloride (yield, 14%).
Melting point: 115.5°–117.0° C.
MS (EI) m/e: 402 (M+)
IR(KBR) cm$^{-1}$: 1728, 1658, 1594, 1454, 1261, 1212, 1022, 761, 727
NMR (DMSO-c$_6$) δ(ppm): 10.86 (1H, brs) 8.23 (1H, d, J=8.3Hz), 7.60 (1H, m), 7.49 (1H, d, J=8.3Hz), 7.10~7.45 (6H, m), 7.18 (1H, s), 5.57 (2H, s), 5.30 (1H, m), 3.90 (2H, m), 2.68 (3H, d, J=5.1Hz), 2.00~2.80 (8H, m)

EXAMPLE 19

Endo-(8-methyl-8-azabicyclo[3.2.1]oct-3-yl) 2-oxo-1-phenyl-1,2-dihydro-4-quinolinecarboxylate (Compound 19)

Compound 19 was obtained as the hydrochloride (yield, 27%) in a manner similar to Example 1 except for using 2-oxo-1-phenyl-1,2-dihydro-4-quinolinecarboxylic acid as synthesized according to the method [Ber., 71, 387 (1938)] instead of Compound a and changing the reaction time from an hour to 3 hours.
Melting point: 128.5°–129.5° C.
MS (EI) m/e: 388 (M+)
IR(KBr) cm$^{-1}$: 1726, 1658, 1589, 1448, 1243, 1224, 1131, 1022, 767, 707
NMR(DMSO-d$_6$) δ(ppm): 11.03(brs), 8.23 (1H, d, J=6.8Hz), 7.40~7.80 (4H, m), 7.25~7.45 (3H, m), 7.14 (1H, s), 6.60 (1H, d, J=8.5Hz), 5.32 (1H, m), 3.91 (2H, m), 2.68 (3H, s), 2.0~3.0 (8H, m)

EXAMPLE 20

Endo-(8-methyl-8-azabicyclo[3.2.1]oct-3-yl) 1-(n-butyl)-3-ethyl-2-oxo-1,2-dihydro-4-quinolinecarboxylate (Compound 20)

1-n-Butyl-3-ethyl-2-oxo-1,2-dihydro-4-quinolinecarboxylic acid was obtained (yield, 57%, 38%) in a manner similar to Reference example 1 except for using Compound d obtained in Reference Example 3 instead of 2-hydroxy-4-quinolinecarboxylic acid and changing the reaction condition of 30 minutes and room temperature in the second step to a reaction condition of 36 hours and heat-reflux. The obtained carboxylic acid in place of Compound a was treated in a manner similar to Example 1 to give Compound 20 as the hydrochloride (yield, 45%).
Melting point: 128.0°–129.0° C.
MS (EI) m/e: 396 (M+)
IR(KBR) cm$^{-1}$: 1741, 1651, 1643, 1601, 1453, 1309, 1219, 1080, 1025, 749
NMR(DMSO-d$_6$) δ(ppm): 10.89 (1H, brs), 7.56~7.73 (2H, m), 7.50 (1H, d, J=8.1Hz), 7.31 (1H, m), 5.44 (1H, m), 4.29 (2H, t, J=7.7Hz), 3.87 (2H, m), 2.66 (3H, s), 2.53 (2H, q, J=7.3Hz), 1.8~2.9 (8H, m), 1.63 (2H, m), 1.42 (2H, m), 1.13 (3H, t, J=7.3Hz). 0.95 (3H, t, J=7.3Hz)

EXAMPLE 21

Endo-(8-methyl-8-azabicyclo[3.2.1]oct-3-yl) 1-(n-butyl)-6-methyl-2-oxo-1,2-dihydro-4-quinolinecarboxylate (Compound 21)

1-(n-Butyl)-6-methyl-2-oxo-1,2-dihydro-4-quinolinecarboxylic acid was obtained (yield, 30%, 100%) in a manner similar to Reference Example 1 except for using Compound e obtained in Reference example 4 instead of 2-hyroxy-4-quinolinecarboxylic acid. The obtained carboxylic acid in place of Compound a was treated in a manner similar to Example 1 to give compound 21 as the hydrochloride (yield, 12%).
Melting point: 121.5°–122.0° C.
MS (EI) m/e: 382 (M+)
IR(KBr) cm$^{-1}$: 1722, 1645, 1585, 1249, 1164, 1077, 1028
NMR (DMSO-d$_6$) δ(ppm) 11.01 (1H, brs), 8.00 (1H, s), 7.55 (2H, s), 7.02 (1H, s), 5.27 (1H, m), 4.26 (2H, t, J=7.6Hz), 3.89 (2H, m), 2.67 (3H, s), 2.39 (3H, s), 1.95~2.90 (8H, m), 1.61 (2H, m), 1.40 (2H, m), 0.93 (3H, t, J=7.3 Hz)

EXAMPLE 22

Endo-N-(8-methyl-8-azabicyclo[3.2.1]oct-3-yl) 1-(n-butyl)-4-hydroxy-2-oxo-1,2-dihydro-1,8-naphthyridine-3-carboxylate (Compound 22)

Ethyl 1-(n-butyl)-4-hydroxy-2-oxo-1,2-dihydro-1,8-naphthyridine-3-carboxylate (yield, 100%, 69%) was obtained in a manner similar to Reference Example 2 except for using methyl 2-(n-butylamino)nicotinate as synthesized according to the method described in J. Org. Chem., 39, 1803 (1974) instead of methyl 2-anilinonicotinate. Then, a mixture of 1.45 g (5.00 mmols) of the carboxylate, 6.10 g (43.20 mmols) of tropine and 100 ml of xylene was heated under reflux for 20 minutes. After completion of the reaction, an aqueous saturated sodium bicarbonate solution was added to the resulting solution followed by extraction with water twice. The aqueous layers were combined and aqueous dil. hydrochloric acid solution was added to render the solution weakly acidic. After extracting with chloroform, the extract was dried over anhydrous sodium sulfate. The solvent was evaporated under reduced pressure to give 1.53 g (yield, 79%) of Compound 22 (yield, 79%).

After 0.46 g (3.96 mmols) of fumaric acid was added to a solution of 1.53 g of Compound 22 in a solvent mixture of isopropyl alcohol and acetone, the mixture was stirred at room temperature. n-Hexane was added to the solution at room temperature with stirring. The precipitated crystals were filtered and dried to give 0.29 g (yield, 15%) of Compound 22 as the fumarate.

Melting point: 123.0°-125.0° C.
MS (EI) m/e: 3 8 5 (M+)
IR(KBr) cm$^{-1}$: 3430(br), 1668, 1620, 1586, 1470, 1407, 1323, 1163, 1024, 973, 799, 777
NMR(DMSO-d$_6$) δ(ppm): 8.46 (1H, d, J=4.8Hz), 8.26 (1H, d, J=7.6Hz), 7.07(1H, m), 6.62 (2H, s), 5.03(1H, m), 4.24(2H, t, J=7.3Hz), 3.82(2H, m), 2.69 (3H, s), 1.85~2.80 (8H, m), 1.56 (2H, m), 1.31(2H, m), 0.90 (3H, t, J=7.3Hz)

EXAMPLE 23

Endo-(8-methyl-8-azabicyclo[3.2.1]oct-3-yl) 1-(n-butyl)-4-hydroxy-2-oxo-1,2-dihydro-3-quinolinecarboxylate (Compound 23)

A mixture of 0.90 g (3.11 mmols) of ethyl 1-(n-butyl)-4-hydroxy-2-oxo-1,2-dihydro-3-quinolinecarboxylate [J. Heterocyclic Chem., 16, 1605 (1979)], 3.30 g (23.37 mmols) of tropine and 50 ml of xylene was heated under reflux for 1.5 hours. After completion of the reaction, an aqueous saturated sodium bicarbonate solution was added to the resulting solution followed by extraction with water twice. The aqueous layers were combined and aqueous dil. hydrochloric acid solution was added to the solution for neutralization. After extracting with chloroform, the extract was dried over anhydrous sodium sulfate. The solvent was evaporated under reduced pressure to give 0.71 g (yield, 59%) of Compound 23.

After 0.21 g (1.81 mmols) of fumaric acid was added to 30 ml of a solution of 0.71 g of Compound 23 in acetone, the mixture was stirred at room temperature. The precipitated crystals were filtered and dried to give 0.29 g (yield, 31%) of Compound 23 as fumarate.

Melting point: 163.0°-164.0° C.
MS (EI) m/e: 384 (M+)
IR(KBr) cm$^{-1}$: 3420(br), 1657, 1619, 1562, 1497, 1408, 1323, 1171, 1023, 982, 766, 754
NMR (DMSO-d$_6$) δ(ppm) 8.02 (1H, d, J=8.1Hz), 7.51 (1H, m), 7.30 (1H, d, J=8.4Hz), 7.08 (1H, m), 6.59 (2H, s), 5.06 (1H, m), 4.09 (2H, t, J=7.1Hz), 3.78 (2H, m), 2.67 (3H, s), 1.85~2.80 (8H, m), 1.54 (2H, m), 1.37(2H, m), 0.92 (3H, t, J=7.2Hz)

EXAMPLE 24

Endo-(8-methyl-8-azabicyclo[3.2.1]oct-3-yl) 4-hydroxy-2-oxo-1-phenyl-1,2-dihydro-1,8-naphthylidine-3-carboxylate (Compound 24)

A mixture of 1.01 g (3.25 mmols) of Compound c obtained in Reference Example 2, 3.00 g (21.24 mmols) of tropine and 40 ml of xylene was heated under reflux for 20 minutes. After cooling, the crystals were taken by filtration and then triturated with chloroform several times. Drying gave 0.73 g (yield, 55%) of Compound 24.

Melting point: 268.0°-270.0° C.
MS (EI) m/e: 405 (M+)
IR(KBr) cm$^{-1}$: 3400(br), 1677, 1614, 1594, 1529, 1466, 1393, 1204, 1106, 1080, 1045, 1031, 975, 930, 798, 719
NMR(DMSO-d$_6$) δ(ppm): 8.24 (1H, d, J=7.7Hz), 8.14 (1H, d, J=4.6Hz), 7.35~7.50 (2H, m), 7.31 (1H, m), 7.05~7.20 (2H, m), 6.99 (1H, m), 4.99 (1H, m), 3.70 (2H, m), 2.50 (3H, s), 1.85~2.75 (8H, m)

EXAMPLE 25

Endo-N-(8-methyl-8-azabicyclo[3.2.1]oct-3-yl)-2-hydroxy-4-quinolinecarboxamide (Compound 25)

Compound 25 was obtained as the fumarate (yield, 23%,, 100%).in a manner similar to Example 6 except for using 2-hydroxy-4-quinolinecarboxylic acid instead of Compound a.

Melting point: 231.8 235.2° C.
MS (EI) m/e: 311 (M+)
IR(KBr) cm$^{-1}$: 3240(br), 3015, 1668, 1635, 1538, 1431, 1091, 973, 754, 637
NMR (DMSO-d$_6$) δ(ppm): 11.89 (1H, brs), 8.59 (1H, d, J=4.1Hz), 7.68 (1H, d, J=8.1Hz), 7.53(1H, m), 7.36(1H, d, J=7.6Hz), 7.19(1H, m), 6.51(2H, s), 6.46 (1H, s), 4.01(1H, m), 3.54 (2H, m), 2.50 (3H, s), 1.97~2.56 (8H, m)

EXAMPLE 26

Endo-N-(8-methyl-8-azabicyclo[3.2.1]oct-3-yl)-1-(n-butyl)-3-ethyl-2-oxo-1,2-dihydro-4-quinolinecarboxamide (Compound 26)

1-(n-Butyl)-3-ethyl-2-oxo-1,2-dihydro-4-quinolinecarboxylic acid was obtained (yield, 57%, 38%) in a manner similar to Reference Example 1 except for using Compound d obtained in Reference Example 3 instead of 2-hydroxy-4-quinolinecarboxylic acid and changing the reaction conditions of 30 minutes and room temperature in the second step to a reaction condition of 36 hours and heat-reflux. The obtained carboxylic acid in place of Compound a was treated in a manner similar to Example 6 to give Compound 26 as the fumarate (yield, 63%, 73%).

Melting point: 155.9°-158.8° C.
MS (EI) m/e: 395 (M+)
IR(KBr) cm$^{-1}$: 2960, 1629, 1589, 1457, 982, 754
NMR (DMSO-d$_6$) δ(ppm): 8.71 (1H, d, J=4.4Hz), 7.54~7.63 (2H, m), 7.59 (1H, d, J=7.6Hz), 7.27 (1H, d, J=7.6Hz), 6.53 (2H, s), 4.23~4.33 (2H, m), 4.13 (1H, m), 3.61 (2H, m), 3.55 (3H, s), 1.91~2.58 (10H, m), 1.61 (2H, m), 1.42 (2H, m), 1.12 (3H, t, J=7.2Hz), 0.96 (3H, t, J=7.2Hz)

EXAMPLE 27

Endo-N-(8-methyl-8-azabicyclo[3.2.1]oct-3-yl)-2-oxo-1-phenyl-1,2-dihydro-4-quinolinecarboxamide (Compound 27)

Compound 27 was obtained as the fumarate (yield, 55%, 92%) in a manner similar to Example 6 except for using 2-oxo-1-phenyl-1,2-dihydro-4-quinolinecarboxylic acid as synthesized by a modification of the method described in Ber., 71, 387 (1938) instead of Compound a.

Melting point: 251.2°–256.2° C.
MS (EI) m/e: 387 (M+)
IR(KBr) cm$^{-1}$: 3300(br), 1640, 1587, 1451, 1292, 1088, 748
NMR(DMSO-d$_6$) (ppm): 8.69 (1H, d, J=4.4Hz), 7.77 (1H, d, J=8.0 Hz), 7.55~7.68(3H, m), 7.46(1H, m), 7.25~7.31(3H, m), 6.64(2H, s), 6.57(1H, d J=8.3Hz), 6.49 (1H, s), 4.05 (1H, m), 3.45 (2H, m), 2.44 (3H, s), 1.90~2.51 (8H, m)

EXAMPLE 28

Endo-N-(8-methyl-8-azabicyclo[3.2.1]oct-3-yl)-3-hydroxy-1-methyl-2-oxo-1,2-dihydro-4-quinolinecarboxamide (Compound 28)

Compound 28 was obtained as the fumarate (yield, 33%, 77%) in a manner similar to Example 6 except for using 3-hydroxy-1-methyl-2-oxo-1,2-dihydro-4-quinolinecarboxylic acid [Chem. Ber., 96, 1234 (1963)] instead of Compound a.

Melting point: 230.0°–236.0° C.
MS (EI) m/e: 341 (M+)
IR(KBr) cm$^{-1}$: 3400(br), 1625, 1457, 1283, 1249, 1219, 982, 752, 647
NMR(CF$_3$COOD) δ(ppm) 7.25~7.88 (5H, m), 7.12 (2H, s), 4.63 (1H, m), 4.17 (3H, s), 4.12 (2H, m), 3.02 (3H, s), 2.51~3.00 (8H, m)

EXAMPLE 29

Endo-N-(8-methyl-8-azabicyclo[3.2.1]oct-3-yl)-1-n-butyl-3-hydroxy-2-oxo-1,2-dihydro-4-quinolinecarboxamide (Compound 29)

Compound 29 was obtained as the fumarate (yield, 42%, 73%) in a manner similar to Example 6 except for using 1-(n-butyl)-3-hydroxy-2-oxo-1,2-dihydro-4-quinolinecarboxylic acid as synthesized according to the method described in Chem. Ber., 96, 1234 (1963) instead of Compound a.

Melting point: 199.9°–207.0° C.
MS (EI) m/e: 383 (M+)
IR(KBr) cm$^{-1}$: 3390(br), 1674, 1632, 1603, 1536, 1463, 1425, 1399, 1276, 1231, 1173, 1037, 733
NMR (CF$_3$COOD ) δ(ppm) 7.70~7.88 (4H, m), 7.50 (1H, m), 7.12 (2H, s), 4.73 (1H, m), 4.59 (2H, t, J=7.4Hz), 4.12 (2H, m), 3.02 (3H, s), 2.52~2.96 (8H, m), 1.88~2.07 (2H, m), 1.52~1.74 (2H, m), 1.09 (3H, t, J=7.4Hz)

EXAMPLE 30

Endo-N-(8-methyl-8-azabicyclo[3.2.1]oct-3-yl)-4-hydroxy-2-oxo-1-phenyl-1,2-dihydro-3-quinolinecarboxamide (Compound 30)

Ethyl 4-hydroxy-2-oxo-1-phenyl-1,2-dihydro-3-quinolinecarboxylate was obtained (yield, 97%, 84%) in a manner similar to Reference Example 2 except for using methyl N-phenylanthranilate instead of methyl 2-anilinonicotinate. The obtained carboxylate in place of ethyl 1-(n-butyl)-4-hydroxy-2-oxo-1,2-dihydro-3-quinolinecarboxylate was treated in a manner similar to Example 11 to give Compound 30 as the fumarate (yield, 75%, 63%).

Melting point: 252.6°–256.7° C.
MS (EI) m/e: 403 (M+)
IR(KBr) cm$^{-1}$: 3450(br), 1629, 1554, 1483, 1405, 1353, 1268, 772, 737, 704
NMR (DMSO-d$_6$) δ(ppm): 10.80 (1H, brs), 8.15 (1H, d, J=8.1Hz), 7.55~7.72 (4H, m), 7.31~7.44(3H, m), 6.63(2H, s), 6.56(1H, d, J=8.7Hz), 4.19(1H, m), 3.83 (2H, m), 2.66 (3H, s), 1.97~2.71 (8H, m)

EXAMPLE 31

Endo-N-(9-methyl-9-azabicyclo[3.3.1]non-3-yl)-4-hydroxy-2-oxo-1-phenyl-1,2-dihydro-3-quinolinecarboxamide (Compound 31)

Ethyl 4-hydroxy-2-oxo-1-phenyl-1,2-dihydro-3-quinolinecarboxylate was obtained (yield, 97%, 84%) in a manner similar to Reference Example 2 except for using methyl N-phenylanthranilate instead of methyl 2-anilinonicotinate. The obtained carboxylate in place of ethyl 1-(n-butyl)-4-hydroxy-2-oxo-1,2-dihydro-3-quinolinecarboxylate was treated in a manner similar to Example 11 except for using Endo-9-methyl-9-azabicyclo[3.3.1]non-3-yl-amine [Japanese Published Unexamined Patent Application No. 67284/84] instead of Endo-8-methyl-8-azabicyclo[3.2.1]oct-3-yl-amine to give Compound 31 as the fumarate (yield, 67%, 83%).

Melting point: 147.7°–160.2° C.
MS (EI) m/e: 418 (M+)
IR(KBr) cm$^{-1}$: 3410(br), 1644, 1627, 1562, 1541, 666

EXAMPLE 32

Endo-N-(8-methyl-azabicyclo[3.2.1]oct-3-yl)-1-(butyl)-4-hydroxy-2-oxo-1,2-dihydro-1,8-naphthyridine-3-carboxamide (Compound 32)

Ethyl 1-(n-butyl)-4-hydroxy-2-oxo-1,2-dihydro-1,8-naphthyridine-3-carboxylate was obtained (yield, 100%, 69%) in a manner similar to Reference Example 2 except for using methyl 2-(n-butylamino)nicotinate as synthesized according to the method described in J. Org. Chem., 39, 1803 (1974) instead of methyl 2-anilinonicotinate. The obtained carboxylate in place of ethyl 1-(n-butyl)-4-hydroxy-2-oxo-1,2-dihydro-3-quinolinecarboxylate was treated in a manner similar to Example 11 to give Compound 32 as the fumarate (yield, 72%, 48%).

Melting point: 176.3°–182.7° C.
MS (EI) m/e: 384 (M+)
IR(KBr) cm$^{-1}$: 3410(br), 2960, 1633, 1588, 1564, 1481, 1407, 1279, 797, 648
NMR(DMSO-d$_6$) δ(ppm): 10.93 (1H, d, J=6.6Hz), 8.82 (1H, dd, J=4.6, 1.7H z), 8.46 (1H, dd, J=7.8, 1.7Hz), 7.44 (1H, dd, J=7.8, 4.6Hz), 6.64 (2H, s), 2.03~2.73 (8H, m), 1.64 (2H, m), 1.36 (2H, m), 0.93 (3H, t, J=7.3Hz)

EXAMPLE 33

Endo-(8-methyl-8-azabicyclo[3.2.1]oct-3-yl) 4-hydroxy-2-oxo-1,2-dihydro-3-quinolinecarboxylate (Compound 33)

Compound 33 was obtained as the fumarate (yield, 21%, 72%) in a manner similar to Example 11 except for using ethyl 4-hydroxy-2-oxo-3-quinolinecarboxylate [J. Pharm. Sci., 54, 792 (1965)] instead of ethyl 1-(n- butyl)-4-hydroxy-2-oxo-1,2-dihydro-3-quinolinecarboxylate and tropine instead of Endo-8-methyl-8-azabicyclo[3.2.1]oct-3-yl-amine.

Melting point: 250.7°–254.9° C.

MS (EI) m/e: 329 (M+)

IR(KBr) cm$^{-1}$: 3410(br), 3000, 1656, 1413, 1277, 1232, 646

NMR(DMSO-d$_6$) δ(ppm) 11.49 (1H, brs), 7.94 (1H, d, J=7.9Hz), 7.63 (1H, m), 7.28 (1H, d, J=8.4Hz), 7.21 (1H, m), 6.63 (2H, s), 5.28 (1H, m) 3.87 (2H, m), 2.51(3H, s), 2.02~2.64 (8H, m)

EXAMPLE 34

Endo-N-(8-methyl-8-azabicyclo[3.2.1]oct-3-yl)-4-hydroxy-2-oxo-1,2-dihydro-3-quinolinecarboxamide (Compound 34)

Compound 34 was obtained as the fumarate (yield, 91%) in a manner similar to Example 11 except for using ethyl 4-hydroxy-2-oxo-3-quinolinecarboxylate [J. Pharm. Sci., 54, 792 (1965)] instead of ethyl 1-(n-butyl)-4-hydroxy-2-oxo-1,2-dihydro-3-quinolinecarboxylate.

Melting point: 275.9°–276.2° C.

MS (EI) m/e: 327 (M+)

IR(KBr) cm$^{-1}$: 3410(br), 1655, 1649, 1558, 1489, 1402, 753

NMR (DMSO-d$_6$) δ(ppm): 11.90 (1H, brs), 11.05 (1H, d, J=5.8Hz), 7.98(1H, d, J=7.9Hz), 7.70 (1H, m), 7.39 (1H, d, J=7.9Hz), 7.30(1H, m), 6.57(2H, s), 4.16 (1H, m), 3.67(2H, m), 2.57 (3H, s), 1.88~2.51 (8H, m)

EXAMPLE 35

Endo-N-(9-methyl-9-azabicyclo[3.3.1]non-3-yl)-4-hydroxy-2-oxo-1,2-dihydro-3-quinolinecarboxamid (Compound 35)

Compound 35 was obtained as the fumarate (yield, 87%) in a manner similar to Example 11 except for using ethyl 4-hydroxy-2-oxo-3-quinolinecarboxylate [J. Pharm. Sci., 54, 792 (1965)] instead of ethyl 1-(n-butyl)-4-hydroxy-2-oxo-1,2-dihydro-3-quinolinecarboxylate and Endo-9-methyl-9-azabicyclo[3.3.1]non-3-yl-amine [Japanese Published Unexamined Patent Application No. 67284/84] instead of Endo-8-methyl-8-azabicyclo[3.2.1]oct-3-yl-amine.

Melting point: 222.4°–223.2° C.

MS (EI) m/e: 341 (M+)

IR(KBr) cm$^{-1}$: 3410(br), 2970, 1652, 1611, 1540, 1325, 1233, 752, 667

EXAMPLE 36

Tablet

Tablet having the following composition is prepared in a conventional manner.

| Compound 1 | 10 mg |
|---|---|
| Lactose | 30 mg |
| Potato starch | 15 mg |
| Polyvinyl alcohol | 1.5 mg |
| Magnesium stearate | 0.5 mg |

EXAMPLE 37

Powder

Powder having the following composition is prepared in a conventional manner.

| Compound 1 | 10 mg |
|---|---|
| Lactose | 150 mg |

EXAMPLE 38

Syrup

Syrup having the following composition is prepared in a conventional manner.

| Compound 1 | 10 mg |
|---|---|
| Refined white sugar | 15 mg |
| Ethyl p-hydroxybenzoate | 20 mg |
| Propyl p-hydroxybenzoate | 5 mg |
| Strawberry flavor | 0.05 cc |

Water is added to the composition to make the whole volume 20 cc.

EXAMPLE 39

Capsule

Capsule having the following composition is prepared in a conventional manner.

| Compound 1 | 10 mg |
|---|---|
| Lactose | 100 mg |
| Magnesium stearate | 2.5 mg |

The above composition is mixed and filled up in a gelatin capsule.

EXAMPLE 40

Injection

Injection having the following composition is prepared in a conventional manner.

| Compound 1 | 10 mg |
|---|---|
| Sodium chloride | 20 mg |

Water is added to the composition to make the whole volume 5 ml (corresponding to one ampoule). Water is previously distilled and sterilized in an autoclave.

REFERENCE EXAMPLE 1

1-(n-Butyl)-2-oxo-1,2-dihydro-4-quinolinecarboxylic acid (Compound a)

While stirring, 5.00 g (26.4 mmols) of 2-hydroxy-4-quinolinecarboxylic acid was added at 0° C. by small portions to 120 ml of a dimethylformamide solution containing 1.39 g (57.9 mmols) of sodium hydride. Under ice cooling, 70 ml of dimethylformamide solution containing 10.7 g (58.0 mmols) of n-butyl iodide was dropwise added to the mixture with stirring. The mixture was stirred at room temperature for further one day. After completion of the reaction, an aqueous saturated sodium bicarbonate solution was added to the reaction mixture followed by extraction with chloroform. After drying over anhydrous sodium sulfate, the solvent was evaporated under reduced pressure. The residue was purified by silica gel column chromatography (eluting solvent: hexane/ethyl acetate=7/1). From the corresponding fraction, 2.05 g (yield; 26%) of 1-(n-butyl)-4-(n-butyloxycarbonyl)-2-oxo-1,2-dihydroquinoline (Compound b) was obtained.

A mixture of 2.04 g (6.77 mmols) of Compound b, 0.54 g of sodium hydroxide, 40 ml of water and 40 mt of dioxane was stirred at room temperature for 30 minutes. After concentration under reduced pressure, the residue was purified by silica gel column chromatography (eluting solvent: chloroform/methanol=5/1) to give 1.44 g (yield: 87%) of Compound a.

Compound b:
NMR (CDCl₃) δ(ppm) 8.35(1H, d, J=8.1Hz) 6.9~7.8 (4H, m) 3.9~4.7 (4H, m), 0.5~2.1 (14H, m)

Compound a:
NMR(DMSO-d₆) δ(ppm) 8.31 (1H, d, J=8.1Hz) 7.30~7.75 (2H, m) 6.95~7.30 (1H, m) 6.61 (1H, s), 4.23 (2H, t, J=7Hz), 1.05~1.90 (4H, m), 0.93 (3H, t ,J=6.4Hz)

REFERENCE EXAMPLE 2

Ethyl 4-hydroxy-2-oxo-1-phenyl-1,2-dihydro-1,8-naphthyridine-3-carboxylate (Compound c)

While heating a mixture of 15.3 g (67.0 mmols) of methyl 2-anilinonicotinate [J. Org. Chem., 39, 1803 (1974)], 150 ml of 1,2-dichloroethane and 15 ml of dioxane at 80° C. with stirring, 24.1 mi (201.0 mmols) of trichloromethyl chloroformate was dropwise added to the mixture over an hour. The mixture was stirred at 90° C. for further 90 minutes. After cooling, 0.75 g of activated carbon was added and the mixture was stirred at 90° C. for 30 minutes. After removing insoluble matters by filtration, the filtrate was concentrated under reduced pressure to give 15.9 g (yield: 99%) of 2,4-dioxo-1-phenyl-1,4-dihydro-2H-pyrido[2,3-d]oxazine.

NMR (CDCl₃) δ(ppm) 8.3~8.6 (2H, m), 7.0~7.7 (6H, m)

While stirring a mixture of 4.00 g (16.7 mmols) of the compound described above and 25.3 ml (166.6 mmols) of diethyl malonate at room temperature, 0.48 g (20.0 mmols) of sodium hydride was added to the mixture. The mixture was stirred for further 2.5 hours with heating at 150° C. After completion of the reaction, 100 ml of ethyl acetate was added to the reaction mixture followed by sonication. The precipitated crystals were filtered By adding 200 ml of water to the crystals, the crystals were dissolved. While stirring at room temperature, conc. hydrochloric acid was added to the solution to adjust pH to 0.1 to 0.2. The precipitated crystals were filtered. After washing with water and drying, 4.30 g (yield: 83%) of Compound c was obtained.

NMR(DMSO-d₆) δ(ppm) 8.49 (1H, dd, J=4.8, 1.8Hz), 8.45 (1H, dd, J=7.9, 1.8Hz), 7.37~7.62 (3H, m), 7.32 (1H, dd, J=7.9, 4.8 Hz), 7.23 (2H, m), 4.33 (2H, q, J=7.1Hz), 1.29 (3H, t, J=7.1Hz)

REFERENCE EXAMPLE 3

3-Ethyl-2-oxo-1,2-dihydro-4-quinolinecarboxylic acid (Compound d)

A mixture of 10.4 g (70.7 mmols) of isatin, 60 m% of butyric anhydride and 2 ml of pyridine was stirred with heating at 140° C. for 30 minutes. After cooling, the solution was poured onto water. While further cooling, dil. sodium hydroxide aqueous solution was added to the solution to render the solution alkaline. The solution was heated under reflux for 30 minutes. After cooling, dil. hydrochloric acid was added to render the solution acidic. The precipitated crystals were filtered, washed with water and dried to give 3.96 g (yield, 26%) of Compound d.

NMR (CDCl₃) δ(ppm) 7.05~7.70 (4H, m), 2.53 (2H, J=7.3Hz) 1.20 (3H, t, J=7.3Hz)

REFERENCE EXAMPLE 4

6-Methyl-2-oxo-1,2-dihydro-4-quinolinecarboxylic acid (Compound e)

With stirring at 0° C., 8.06 g (50.0 mmols) of 5-methylisatin was added by small portions to a solution of 2.00 g (50.0 mmols) of sodium hydride in toluene. While stirring under ice cooling, 4.7 ml (50.0 mmols) of acetic anhydride was dropwise added to the mixture followed by heating at 80° C. for further an hour with stirring. After completion of the reaction, an aqueous saturated sodium bicarbonate solution was added to the reaction mixture. The crystals were filtered, washed with water and dried to give 4.84 g (yield, 47%) of 1-acetyl-5-methylisatin.

NMR (CDCl₃) δ(ppm): 8.29 (1H, d, J=8.5Hz), 7.57 (1H, s), 7.52 (1H, d, J 8.5Hz), 2.72 (3H, s), 2.40 (3H, s)

A mixture of 4.84 g (23.7 mmols) of the compound described above and sodium hydroxide aqueous solution was heated under reflux for 30 minutes. After cooling, aqueous dil. hydrochloric acid was added to render the mixture acidic. The precipitated crystals were filtered, washed with water and dried to give 3.61 g (yield, 75%) of the crude product of Compound e.

What is claimed is:

1. A heterocyclic compound represented by general formula (I):

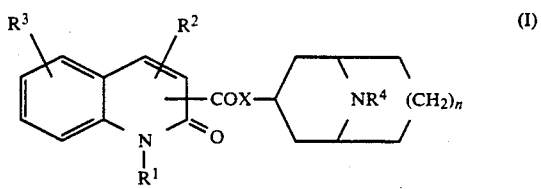

wherein R¹ represents hydrogen, lower alkyl or aryl; R² represents hydrogen, hydroxyl or lower alkyl; X represents —O— or —NH—; R³ represents hydrogen, hydroxyl or lower alkyl; R⁴ represents lower alkyl; and n represents 0 to 1, or a pharmaceutically acceptable salt thereof.

2. The compound according to claim 1, wherein n is 0.

3. The compound according to claim 2, wherein R¹ is lower alkyl; R² is hydrogen; X is —O—; and R³ is hydrogen.

4. The compound according to claim 1, wherein said salt is selected from the group consisting of an acid addition salt, a metal salt and an amino acid addition salt.

5. Endo-(8-methyl-8-azabicyclo[3.2.1]oct-3-yl) 1-(n-butyl)-2-oxo-1,2-dihydro-4-quinolinecarboxylate.

6. A composition useful in the propylatic or therapeutic treatment of vomiting and migraine comprising a pharmaceutical carrier, and as active ingredient an effective amount of the compound as defined by claim 1.

* * * * *